United States Patent
Snyder et al.

(10) Patent No.: US 6,370,428 B1
(45) Date of Patent: Apr. 9, 2002

(54) METHOD FOR CONFIGURING A DEFIBRILLATOR

(76) Inventors: David E. Snyder, 353 Wallace Way NE. #15, Bainbridge Island, WA (US) 98110; Bradford E. Gliner, 4368 230th Way SE., Issaquah, WA (US) 98029; Thomas D. Lyster, 23309 21st Ave. SE., Bothell, WA (US) 98021

( * ) Notice: Subject to any disclaimer, the term of this patent is extended or adjusted under 35 U.S.C. 154(b) by 0 days.

(21) Appl. No.: 09/372,544

(22) Filed: Aug. 11, 1999

(51) Int. Cl.[7] .................................................. A61N 1/39
(52) U.S. Cl. ......................................................... 607/5
(58) Field of Search ............................................. 607/5

(56) References Cited

U.S. PATENT DOCUMENTS

| | | | | |
|---|---|---|---|---|
| 5,944,741 A | * | 8/1999 | Ochs et al. ................. | 607/5 |
| 5,951,484 A | * | 9/1999 | Hoium et al. ............... | 600/515 |
| 6,021,349 A | * | 2/2000 | Arand et al. ................ | 607/5 |
| 6,101,413 A | * | 8/2000 | Olson et al. ................ | 607/5 |
| 6,108,578 A | * | 8/2000 | Bardy et al. ................ | 607/5 |
| 6,141,584 A | * | 10/2000 | Rockwell et al. ............ | 607/5 |

* cited by examiner

*Primary Examiner*—Carl Layno

(57) ABSTRACT

A defibrillator configurable for optimal behavior across a broad spectrum of patients, users, and circumstances is provided. A set of environmental characteristics that represent the patient population, the user population, and the possible circumstances are determined and then applied to a configure algorithm to determine an optimal behavior of the defibrillator as reflected through the set up parameters. The set of environmental characteristics can be entered manually or determined from dispatch data supplied by computerized dispatch systems. The optimal behavior can also be achieved using adaptation algorithms such as fuzzy logic and neural networks that allow the defibrillator to obtain measurements of the environmental characteristics and alter its behavior based on those measurements.

21 Claims, 8 Drawing Sheets

METHOD FOR CONFIGURING A DEFIBRILLATOR

BACKGROUND OF THE INVENTION

This invention relates to electrotherapy circuits and in particular to a method for configuring an external defibrillator based on environmental characteristics.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electrochemical system to re-synchronize itself. Once organized electrical activity is restored, synchronized muscle contractions usually follow, leading to the restoration of cardiac rhythm.

FIG. 1 is an illustration of a defibrillator 10 being applied by a user 12 to resuscitate a patient 14 suffering from cardiac arrest. In cardiac arrest, otherwise known as sudden cardiac arrest, the patient is stricken with a life threatening interruption to their normal heart rhythm, typically in the form of ventricular fibrillation (VF) or ventricular tachycardia (VT) that is not accompanied by a palpable pulse (shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be applied after the onset of VF, the better the chances that the patient 14 will survive the event.

The defibrillator 10 may be in the form of an automatic external defibrillator (AED) capable of being operated by users with a wide variety of skill levels ranging from first responders to physicians, including emergency medical technicians trained in defibrillation (EMT-Ds), police officers, flight attendants, security personnel, occupational health nurses, and firefighters. AEDs can also be used in areas of the hospital where personnel trained in ACLS (advanced cardiac life support) are not readily available.

Having a simple, easily understood user interface in an AED is particularly important in applications where the first responder may have only infrequent need to use the AED. Because training and refresher courses may be relatively infrequent, coupled with a high stress emergency situation in which the AED is designed to be used in, the user interface design is therefore critical.

In more recent AED designs such as the Heartstream Forerunner® defibrillator, the AED functions have been logically grouped into step 1, "power on"; step 2, "analyze"; and step 3, "shock." More sophisticated audio prompts have been added in addition to the visual prompts provided by the LCD display. The transition from step 1 to step 2 may be initiated by the defibrillator, such as upon detection of patient contact between the defibrillation electrodes to begin the ECG analysis as soon as possible. Proceeding from step 2 to step 3 according to the AED personality requires the user to press a shock button upon recognition of a shockable rhythm by the ECG analysis algorithm. In this way, the AED personality is commonly understood to mean semi-automatic rather than fully automatic defibrillation.

The step 1, 2, and 3 methodology, with some variation among manufacturers, is commonly understood and accepted as the AED personality. After step 3, the AED can continue the ECG analysis as a background process to watch for shockable rhythms and alert the user 12.

In FIG. 1 according to step 1 of the AED personality, the defibrillator 10 is turned on and a pair of electrodes 16 is applied across the chest of the patient 14 by the user 12 in order to acquire an ECG signal from the patient's heart. According to step 2 of the AED personality, the defibrillator 10 then analyzes the ECG signal to detect ventricular fibrillation (VF). If VF is detected, the defibrillator 10 signals the user 12 that a shock is advised. According to step 3 of the AED personality, the user 12 then presses a shock button on the defibrillator 10 to deliver the defibrillation pulse to resuscitate the patient 14.

The defibrillator 10 thus forms a nexus between a population of patients 14 and a population of users 12. The behavior of the defibrillator 10 is critical in maximizing both the efficacy of the resuscitation effort and patient safety across the two populations and also across the variety of circumstances in which the defibrillator 10 may be used. It has been found that the behavior of the defibrillator 10 may be optimized according to a set of meaningful parameters across the population of patients 14, the population of users 12, and the various circumstances in which the defibrillator 10 may be employed.

The configuration parameters of the defibrillator 10 that determine the behavior of the defibrillator 10 are often complex and arcane, bearing little resemblance to the environmental characteristics. It would be desirable to be able to map the set of environmental characteristics to the set of configuration parameters to ease the process of configuring the defibrillator 10.

The population of patients 14 spans the entire human population since sudden cardiac arrest (SCA) can potentially affect anyone. The human population can be further categorized using environmental characteristics that have been found to be meaningful for defibrillation and resuscitation purposes. For example, the patient 14 may have a transthoracic impedance ("patient impedance") that spans a range commonly understood to be 20 to 200 ohms. It is desirable that the defibrillator 10 provide an impedance-compensated defibrillation pulse that delivers a desired amount of energy to any patient across the range of patient. The patient's age group, generally categorized as infant, adult, and geriatric, may determine the minimum amount of energy needed for effective defibrillation as well as the appropriate resuscitation protocols that determine how the defibrillator is to be applied. It would be desirable that the behavior of the defibrillator 10 be optimized according to a set of patient characteristics.

The population of users 12 includes first responders with little or infrequent training in the use of defibrillators, designated first responders who may have more frequent training as a secondary part of their jobs, and EMTs, paramedics, and physicians who have higher levels of medical training and more frequent opportunities to use defibrillators. This classification takes into account the level of user (operator) training and as well as the familiarity of the user 12 with the defibrillation process. It would be desirable that the behavior of the defibrillator 10 be optimized according to the type of user 12.

The circumstances in which the defibrillator 10 will be applied will vary widely. Defibrillation could take place in the victim's home, on board an airliner or ship, on the street, or any other of a variety of locations. The geographic location of the defibrillation is an environmental characteristic that substantially affects the time required to get more advanced cardiac care on scene with the patient as well as the transport time needed to get the patient 14 to a hospital. It would be desirable that the behavior of the defibrillator 10 be optimized according to transport time.

In many situations such as a drowning, cardiac arrest is preceded by respiratory arrest. It has been found that cardiopulmonary resuscitation (CPR) is best applied more aggressively before attempting defibrillation in such cases. It is thus desirable that the defibrillator behavior be modified for such applications to emphasize the use of CPR before attempting defibrillation. The application of CPR can be monitored by the defibrillator 10 with feedback given to the user 12. In U.S. application Ser. No. 08/965,347, titled "External defibrillator with CPR prompts and ACLS prompts and Method of Use", filed Jun. 30, 1999 and assigned to the assignee of the present invention, the incorporation of prompts for CPR and other cardiac care is discussed.

The location of the defibrillator such with the staff of a public swimming pool or life guard facility would allow optimization of the defibrillator behavior for resuscitation of drowning victims. It would therefore be desirable that the behavior of the defibrillator 10 can be optimized for maximizing the resuscitation efficacy and patient safety based on the environment characteristics in which the defibrillator 10 is to be applied.

SUMMARY OF THE INVENTION

In accordance with the present invention, a medical device that is configurable for optimal behavior across a broad spectrum of patients, users, and circumstances is provided. The defibrillator is an example of a medical device having a user interface that typically includes front panel buttons, a liquid crystal display (LCD), and an audio speaker. The behavior of the defibrillator as reflected through the user interface is determined according to a set of set up parameters.

A set of environmental characteristics that represent the patient population, the user population, and the possible circumstances are first determined. The environmental characteristics are chosen that are relevant to determining the behavior of the defibrillator as reflected through the user interface.

The set of environment characteristics are then applied to a configure routine to determine an optimal behavior of the defibrillator. Optimal behavior of the defibrillation provides for achieving resuscitation of the patient in a manner which optimizes defibrillation efficacy and patient safety. Other optimal behaviors such as maximizing defibrillator battery life may also be achieved according to application requirements.

Maximizing defibrillation efficacy means that the defibrillation process is as reliable and error free as possible, given the particular patient, user, and circumstance. For example, an inexperienced user will require more frequent and detailed prompts from the defibrillator than a physician. A pediatric patient will typically require different defibrillation protocols such as lower energy levels than an adult patient for maximum defibrillation efficacy and patient safety. A patient suffering from respiratory arrest followed by cardiac arrest requires increased emphasis on CPR.

Maximizing patient safety means that the defibrillation process minimizes the possibility of injury to the patient and as well as to the user. For example, the inexperienced user may not know to refrain from touching the patient when the defibrillator is analyzing the heart rhythm. Such touching and movement introduce measurement artifacts which impede the process of detecting a shockable heart rhythm such as VF. The defibrillator can be adapted with increased user prompts to not touch the patient, adjusting the shock advisory algorithm to be more conservative in detecting shockable rhythms, and increased emphasis on artifact detection.

The optimal behavior can also be achieved using adaptation algorithms such as fuzzy logic and neural networks that allow the defibrillator to obtain measurements of the environmental characteristics and alter its behavior based on those measurements. Monitoring a pattern of usage may uncover differences in the environmental characteristics not anticipated when the defibrillator was originally configured. Providing for a control program that changes the configuration parameters allows the behavior of the defibrillator to be adjusted responsive to new environmental characteristics.

Defibrillators are one example of a medical device that may benefit from the ability to be configured to match the environmental characteristics. Other such medical devices may include cardiac monitors and drug delivery devices.

A feature of the present invention is to provide a method for configuring a medical device based on environmental characteristics.

Another feature of the present invention is to provide a configurable medical device.

A further feature of the present invention is to provide a configurable defibrillator.

Another feature of the present invention is to provide a defibrillator that may be configured according to environmental characteristics.

Another feature of the present invention is to provide a defibrillator capable of adapting to new environmental characteristics.

Other features, attainments, and advantages will become apparent to those skilled in the art upon a reading of the following description when taken in conjunction with the accompanying drawings.

DETAILED DESCRIPTION OF THE INVENTION

Figure 1:
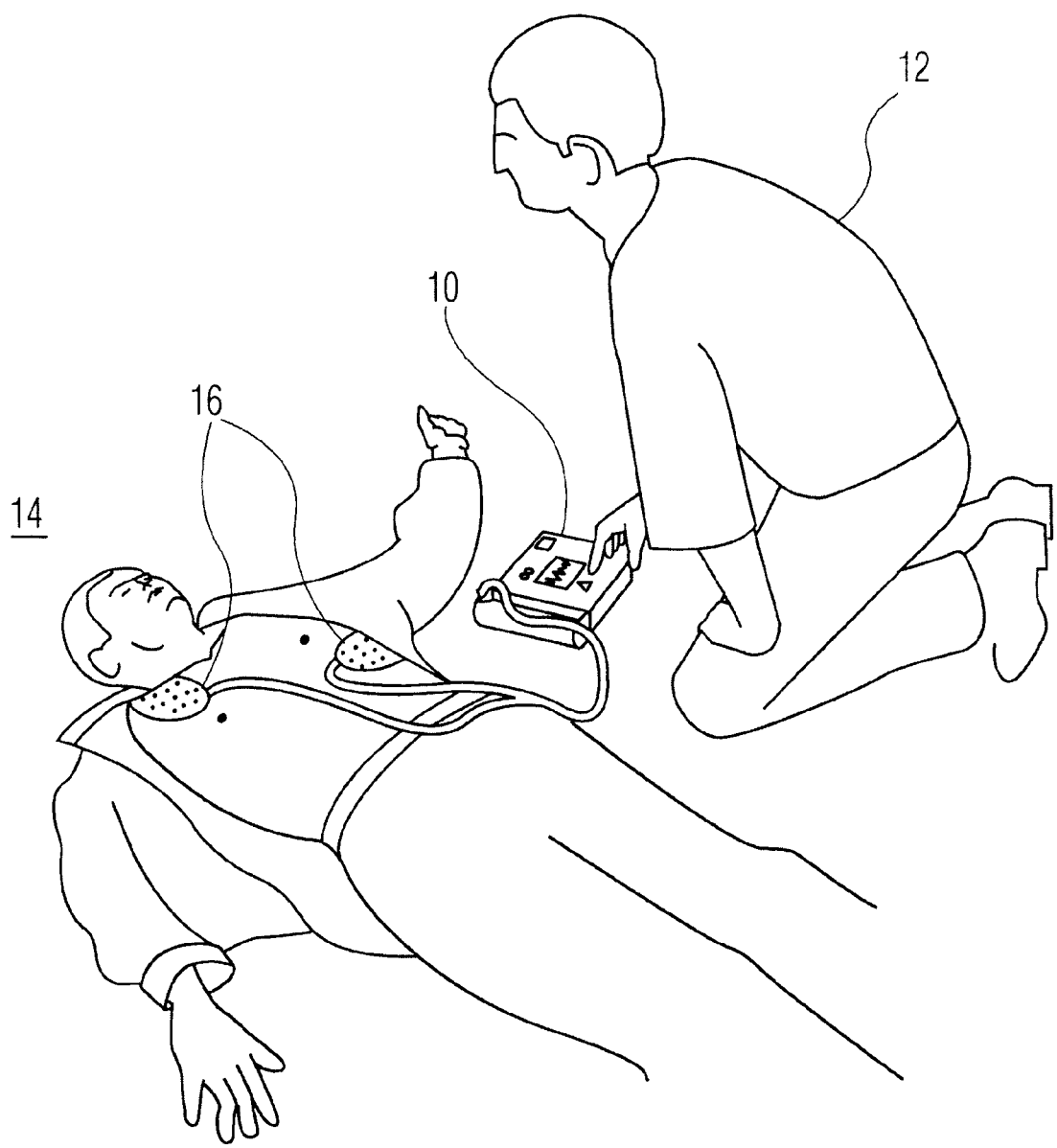
FIG. 1 is an illustration of a typical scenario of a defibrillator being applied by a user to resuscitate a patient suffering from cardiac arrest.
Figure 2:
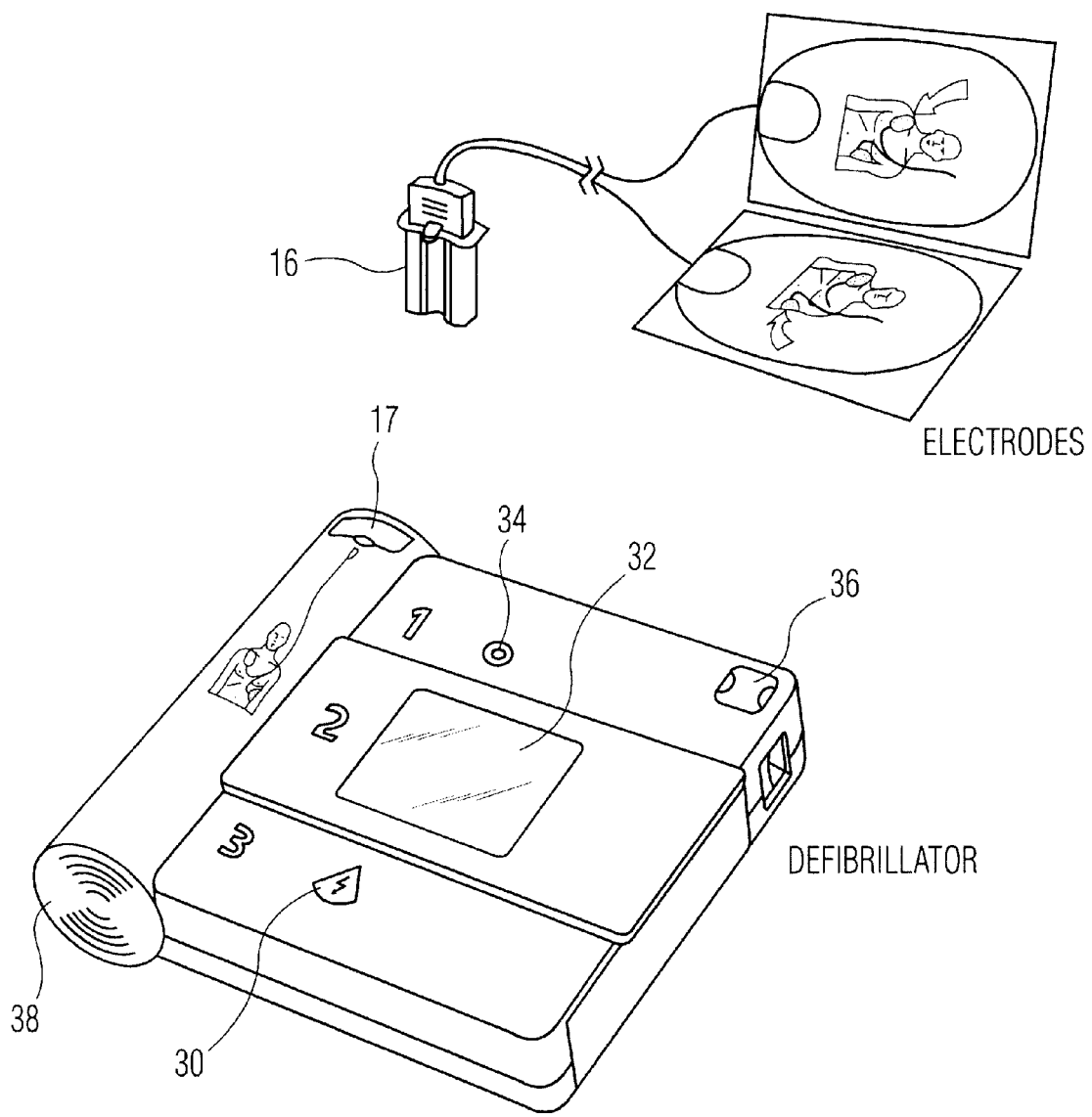
FIG. 2 is an illustration of a typical defibrillator and set of electrodes.

FIG. 2 is an illustration of the defibrillator 10 configured as an automatic external defibrillator (AED). The user interface of the defibrillator 10 includes an on-off button 34. A condition indicator 36 indicates the readiness of defibrillator 10 for use. A display 32, typically implemented with LCD technology, provides for visual prompts to the user 12 and may be used to graphically display ECG waveforms and CPR prompts. A speaker 38 provides for audio prompts such as by voice or tones to the user 12. A shock button 30 is pressed by the user 12 responsive to prompts from the defibrillator 10 such as illuminating the shock button 30 and generating audio prompts. A pair of electrodes 16 is plugged into a jack 17 to couple the patient 14 to the defibrillator 10.

Figure 3:
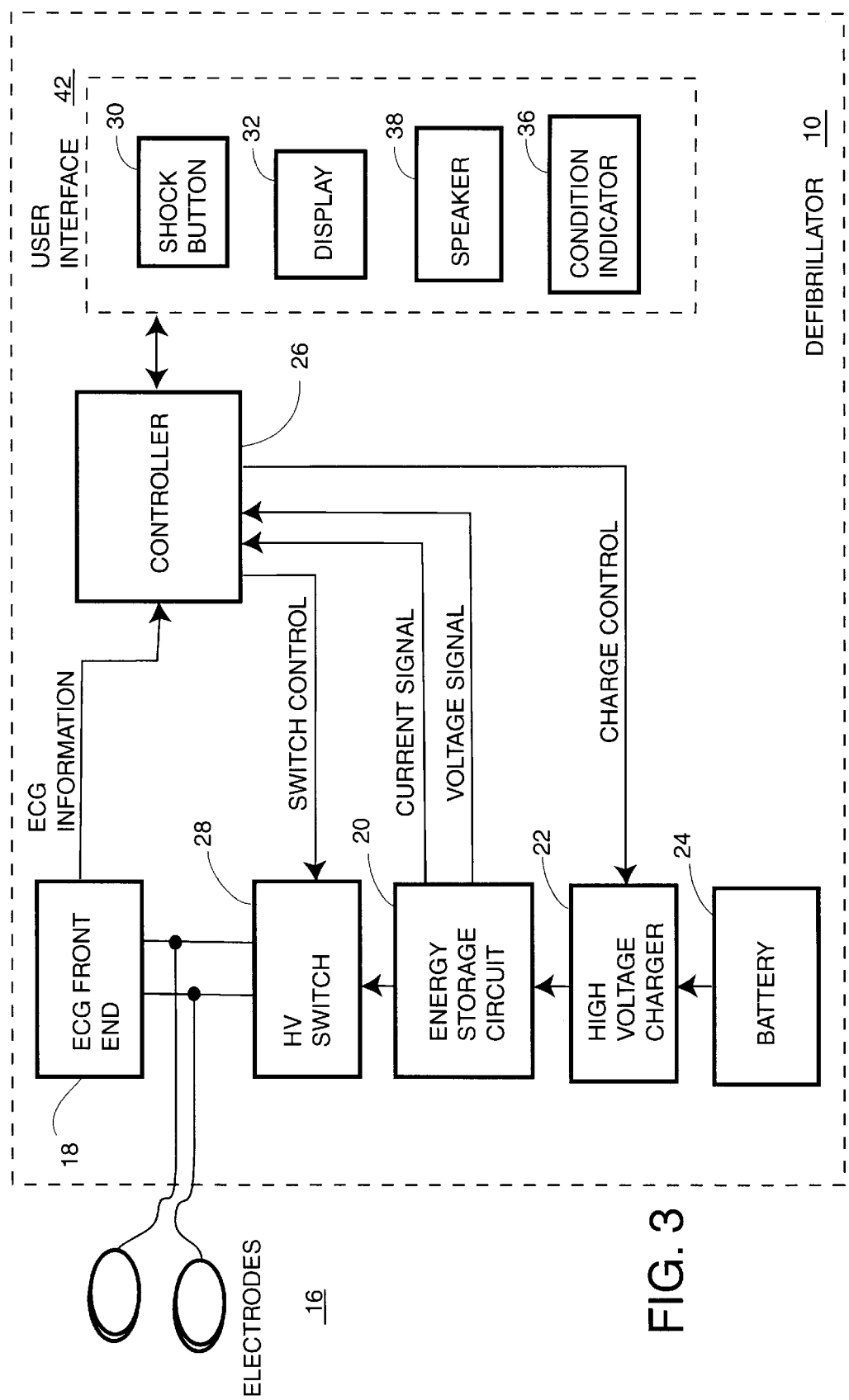
FIG. 3 is a simplified block diagram of the defibrillator.

FIG. 3 is a simplified block diagram of a defibrillator 10 according to the present invention. The pair of electrodes 16 for coupling to the patient 14 are connected to an ECG front end 18 and further connected to an HV switch 28. The ECG front end 18 provides for detection, filtering, and digitizing of the ECG signal from the patient 14. The ECG signal is in turn provided to a controller 26 which runs a shock advisory algorithm that is capable of detecting ventricular fibrillation (VF) or other shockable rhythm that is susceptible to treatment by electrotherapy.

The shock button 30 is pressed by the user 12 to initiate the delivery of a defibrillation pulse through the pair of electrodes 16 after the controller 26 has detected VF or other shockable rhythm. A battery 24 provides power for the defibrillator 10 in general and in particular for a high voltage charger 22 that charges the capacitors in an energy storage circuit 20. Typical battery voltages are 12 volts or less, while the energy storage circuit 20 may be charged to 1500 volts or more. A charge voltage control signal from the controller 26 determines the charge voltage in the energy storage circuit 20. The shock button 30, display 32, speaker 38, and condition indicator 36 collectively form a user interface 42.

The energy storage circuit 20 is connected to the HV switch 28 which operates to deliver the defibrillation pulse across the pair of electrodes 16 to the patient 14 in the desired polarity and duration response to the switch control signal from the controller 26. The HV switch 28 is preferably constructed using an H bridge to deliver biphasic defibrillation pulses in the preferred embodiment but could readily be adapted to deliver monophasic or multiphasic defibrillation pulses and still realize the benefits of the present invention.

Figure 4:
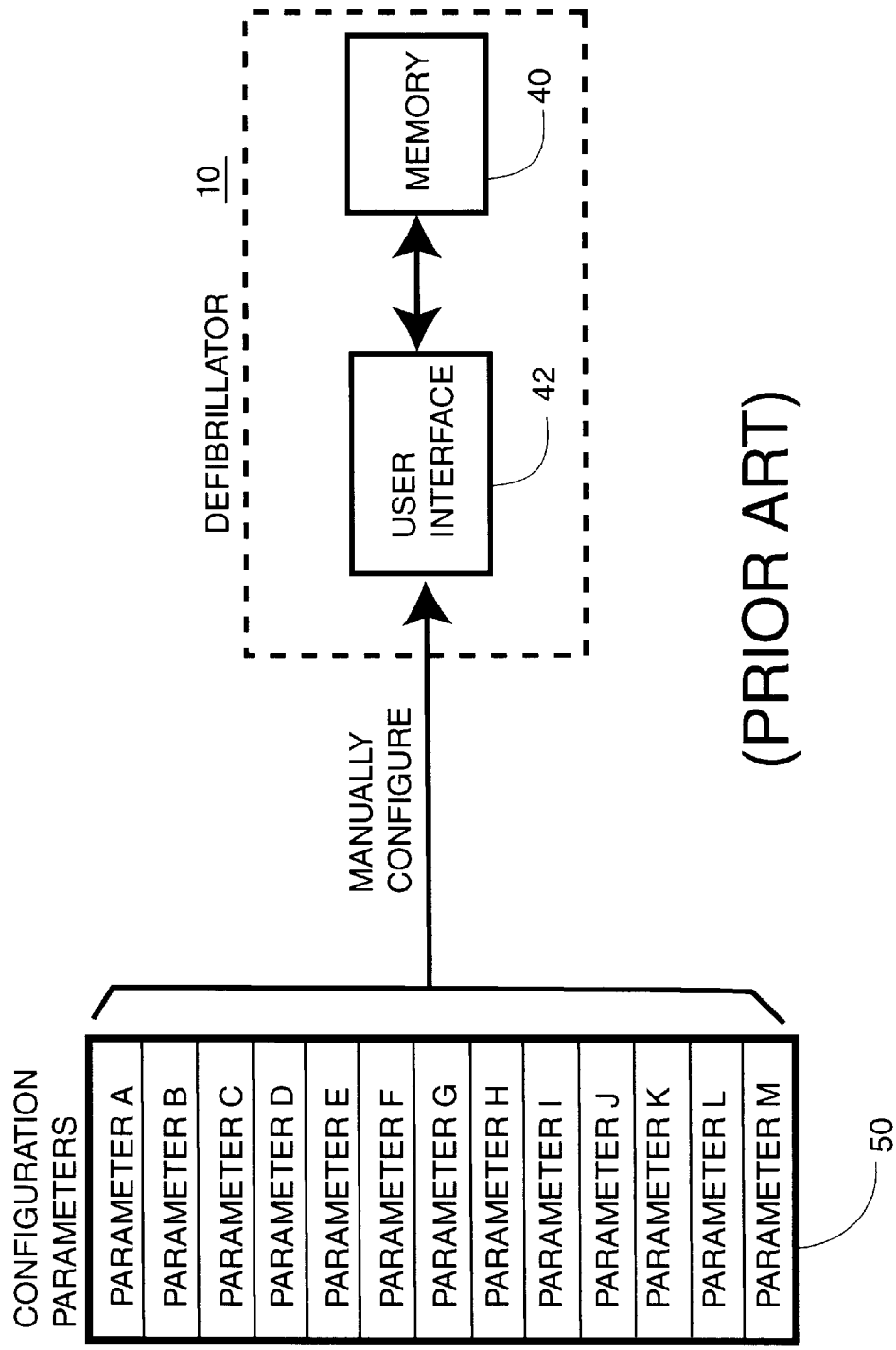
FIG. 4 is an illustration of the process of configuring a defibrillator with a set of configuration parameters according to the prior art.

FIG. 4 illustrates the process of manually configuring the defibrillator 10 according to the prior art. A set of configuration parameters 50, including the parameters A–M shown as an example, are entered individually by setting the user interface 42 to a configuration mode. Each of the configuration parameters 50 defines various set-up options that are particular to the defibrillator 10. For example, speaker volume, ECG display on/off, manual operation enable, defibrillation energy levels over three successive shocks, timeout length to pause for CPR, and so on are all configuration parameters that can be individually changed. Such parameters could be changed using the user interface 42 directly or down-loaded to the defibrillator 10 via a data card, serial port, or infrared ("IrDA") port from a host computer. The set of configuration parameters 50 is then stored in a memory 40 to define the behavior of the defibrillator 10.

The prior art technique of configuring the defibrillator 10 shown in FIG. 4 suffers from the problem of having to change individual parameters which may require referencing product manuals or other user documentation to understand their function as well as their relation to other parameters. Changing one parameter may affect other parameters. At the same time, adapting the defibrillator 10 to new situations is difficult because there is no clear mapping between the environmental characteristics and the set of configuration parameters 50.

Figure 5:
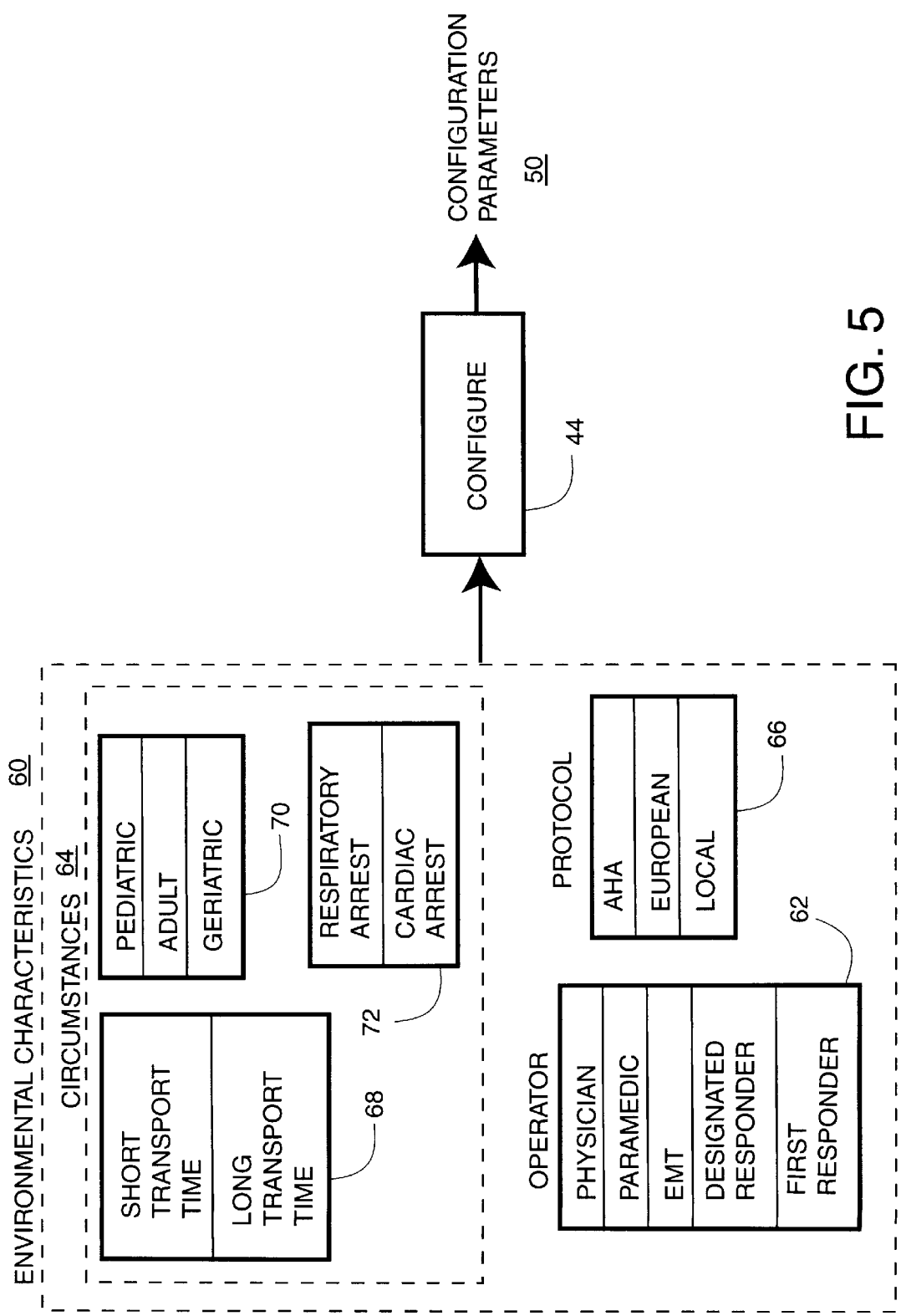
FIG. 5 is an illustration showing process of mapping a set of environmental characteristics to the set of configuration parameters according to the present invention.

FIG. 5 is an illustration showing a process of applying a set of environmental characteristics to a configure routine 44 to obtain the set of configuration parameters 50 according to the present invention. A set of environmental characteristics 60 that include operator type 62, circumstances 64, and protocol 66 are presented in a host computer 46 to a user in order to configure the defibrillator 10. The set of environmental characteristics 60 is chosen to reflect the most relevant characteristics of the environment in which the defibrillator 10 is to be applied that would allow its behavior to be optimized. Optimized behavior means that the defibrillator 10 behaves in a manner that maximizes the chances of successful resuscitation and also maximizes patient safety in a given environment. For example, the chance of successful resuscitation can be maximized both by reducing the chance of error in operating the defibrillator 10 and also by maximizing the speed in which the defibrillator 10 can be deployed. However, speed and error-free operation are typically traded off according to the operator type 62.

The operator type 62 is organized according to a taxonomy of training levels ranging from a highly skilled physician requiring little in the way of guidance from the defibrillator 10 to the first responder who may require substantially more guidance. Such guidance, such as in the form of audible or visual prompts provided by the user interface 42, can add a substantial amount of time to the defibrillation process which, in the case of the operator type 62 as physician, adds little value. The operator type 62 is thus chosen as a one of the set of environmental characteristics 60 because it has been shown to have a strong correlation in determining the optimal behavior of the defibrillator 10.

Similarly, circumstances 64, which may include a variety of factors such as transport time, patient age, and type of arrest, and may have a strong correlation in determining the optimal behavior of the defibrillator 10. Transport time 68, grouped into short and long, may be an important factor in maximizing patient safety. For example, on board an airliner, the defibrillator 10 may be applied in long transport time situations typically exceeding an hour. The defibrillator 10 may be optimized to have a behavior that allows for an ECG monitoring mode to assist in patient care and battery saving features to allow for extended operation.

Patient age 70 is another example of a factor that may have a strong correlation in determining the optimal behavior of the defibrillator 10. It is known that pediatric patients require less defibrillation energy than adult patients. The behavior of the defibrillator 10 in terms of defibrillation energy could then be adjusted downward maximize pediatric patient safety. Geriatric patients on the other hand, could require an entirely different behavior depending on their physiology.

Type of arrest 72 is a further example of a factor that may have strong correlation in determining the optimal behavior of the defibrillator 10. If cardiac arrest is preceded by respiratory arrest, which is commonly found in drowning victims, the chances of successful resuscitation are enhanced through increased emphasis on CPR (cardiopulmonary resuscitation) rather than simply applying a defibrillation pulse. The defibrillator 10, based on the type of arrest 72 typically determined by the anticipated application, could then be optimized to prompt the user to first perform CPR on the patient and act as a monitor in order to provide feedback on the efficacy of the CPR effort.

Protocol 72 is determined by the medical director of the region in which the defibrillator 10 is applied. The medical director may choose from a variety of defibrillation protocols, such as AHA (American Heart Association) protocol, a European protocol, or a local protocol which may be any of a variety of variations. Protocols commonly determine the number of successive defibrillation pulses that may be applied, their respective defibrillation energies, and other factors that must be rigidly adhered to in order for the defibrillator 10 to be acceptable for use in that jurisdiction. Because of the interaction between the protocol and the various other environmental characteristics, the present invention allows for optimization of the defibrillator 10 in conforming with the protocol 66. For example, the protocol 66 may allow for different defibrillation energy levels based on the patient age 64.

The set of environmental characteristics 60 is applied to the configure routine 44 which operates to map the set of environment characteristics 60 to the set of configuration parameters 50. The configure routine 44 is preferably written as a set of software instructions which may be executed by a microprocessor, controller, host computer, or other commonly available processors. The operation of the configure routine 44 is given in more detail below.

Figure 6A:
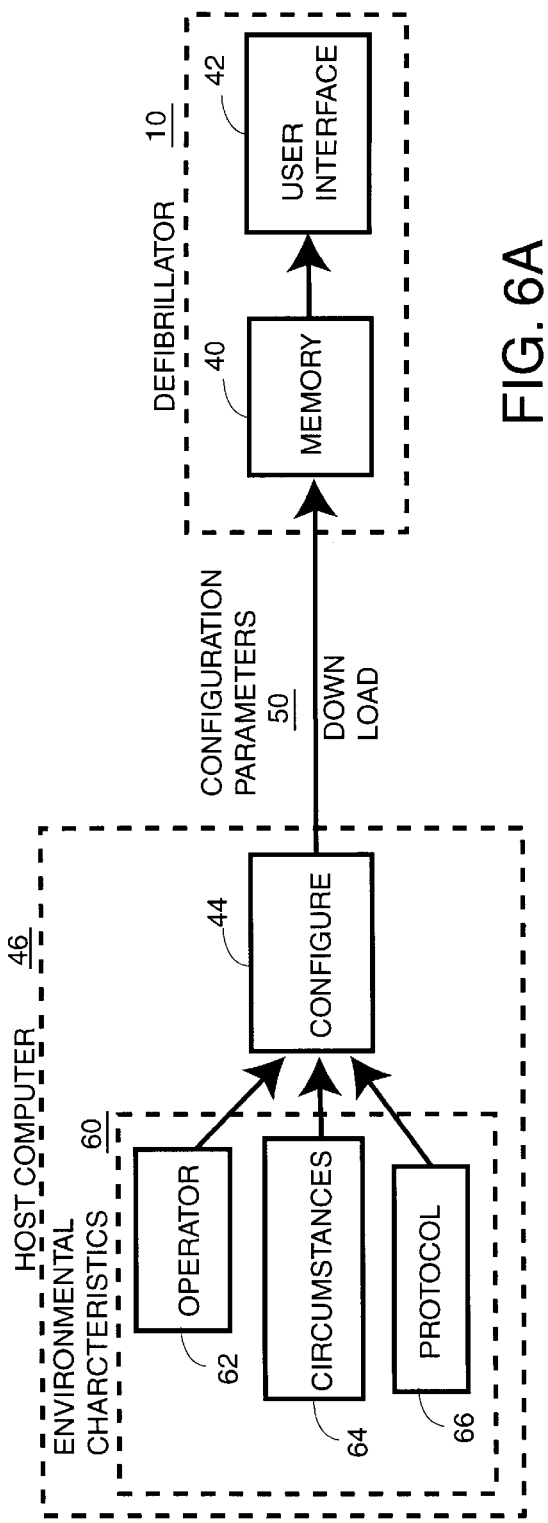
FIGS. 6A and 6B are illustrations of several alternative embodiments of the process of applying a configure algorithm to determine configuration parameters based on environmental characteristics, either in a host computer or in the defibrillator, according to the present invention.
Figure 6B:
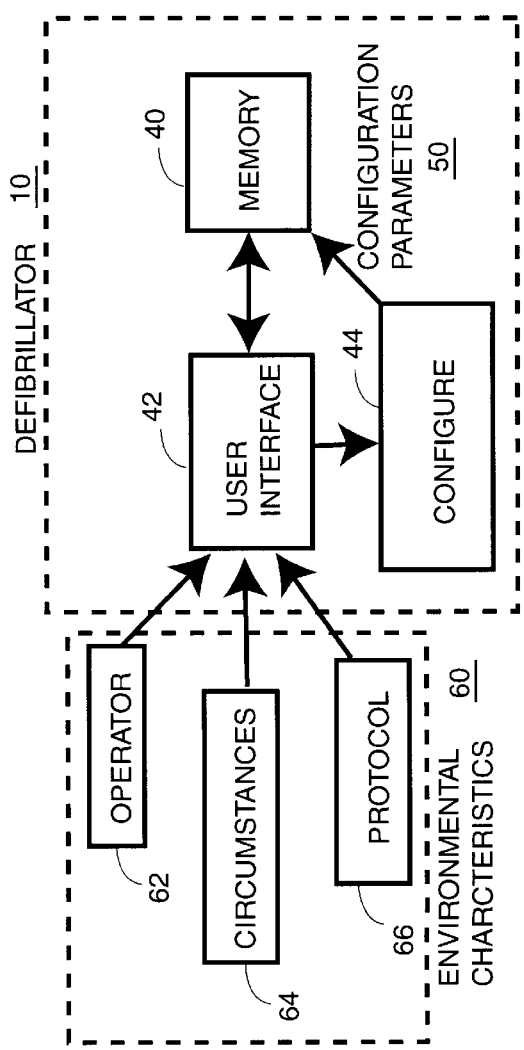

FIG. 6A and 6B illustrate alternative processes of configuring a defibrillator according to the present invention. In FIG. 6A, a host computer 46 running a software program for the configure routine 44 is used to produce the set of configuration parameters 50 which are then downloaded to the defibrillator 10. The environmental characteristics may be entered into the host computer 46 by an operator typically through a graphical user interface (GUI) using techniques commonly known in the art. The download process from the host computer 46 to the defibrillator 10 could take place through any of variety of communication forms, including RS-232 serial bus, IrDA, and universal serial bus (USB) or via an internet or local area network link. The set of configuration parameters 50 would typically reside in a memory 40 within the defibrillator 10 for determining the behavior of the defibrillator 10 through the user interface 42.

The typical application of the host computer 46 is in the case of a medium to large emergency medical service (EMS) that may deploy a large number of defibrillators 10. Maintaining the defibrillators 10 and ensuring their proper behavior is made easier through automated techniques using the host computer 46. At the same time, variations in the defibrillators 10 can be accommodated through their assigned users.

Defibrillators assigned to various departments within an EMS jurisdiction such as the fire department, the police department, and the parks department may each have different behaviors optimized for their situations based on the differences in the set of environmental characteristics 60. For example, differences in the type of operator type 62 among the various groups may be significant. The fire fighter is typically an EMT with relatively frequent exposure to medical emergencies whereas the parks department employee may only be a designated first responder who receives occasional in-service training as part of their job. It may be readily appreciated that an entirely new set of environmental characteristics 60 based on the relevant subsets within an EMS system could be created to optimize the behavior of the defibrillator 10.

In FIG. 6B, the set of environmental characteristics 60 may be entered directly into the defibrillator 10 with the help of the user interface 42. The environmental characteristics are provided to the configure routine 44 which is preferably executed by the controller 26 to obtain the set of configuration parameters 50 which are then stored in the memory 40. The use of the configure routine 44 within the defibrillator 10 allows for adaptive behavior based on differences in the set of environmental characteristics 60.

A defibrillator with AED and manual personalities is discussed in U.S. Pat. No. 6,021,349, titled "Automatic External Defibrillator With Manual Features", issued Oct. 31, 2000, that is assigned to the assignee of the present invention and is incorporated herein by reference. Based on the operator type 62, which was assumed to be either a first responder or an EMT, an expanded set of manual modes is made available to the user. The present invention allows such a mapping of operator type 62 to configuration parameters 50 to be readily determined and more readily modifiable to allow for optimized behavior.

The environmental characteristics 60 can be dynamically applied to the defibrillator 10 for specific situations. The patient circumstances, type of call that was dispatched, and type of operator can be manually entered into the defibrillator 10 via the user interface 42. The environmental characteristics 60 can also be applied to the defibrillator 10 in an automated fashion. Computerized dispatch systems (not shown) commonly employed in many metropolitan areas send dispatch data to mobile data terminals mounted in emergency vehicles. This dispatch data can be dynamically applied to configure the defibrillator 10. The environmental characteristics from the dispatch data could be gathered either by the host computer 46 or applied directly to the defibrillator 10 via a wireless link such as an IrDA port. For example, the dispatch data "pediatric drowning with CPR in progress" could be readily parsed into the set of environmental characteristics 60 which could then be applied to the defibrillator 10 while en route to the scene.

Figure 7:
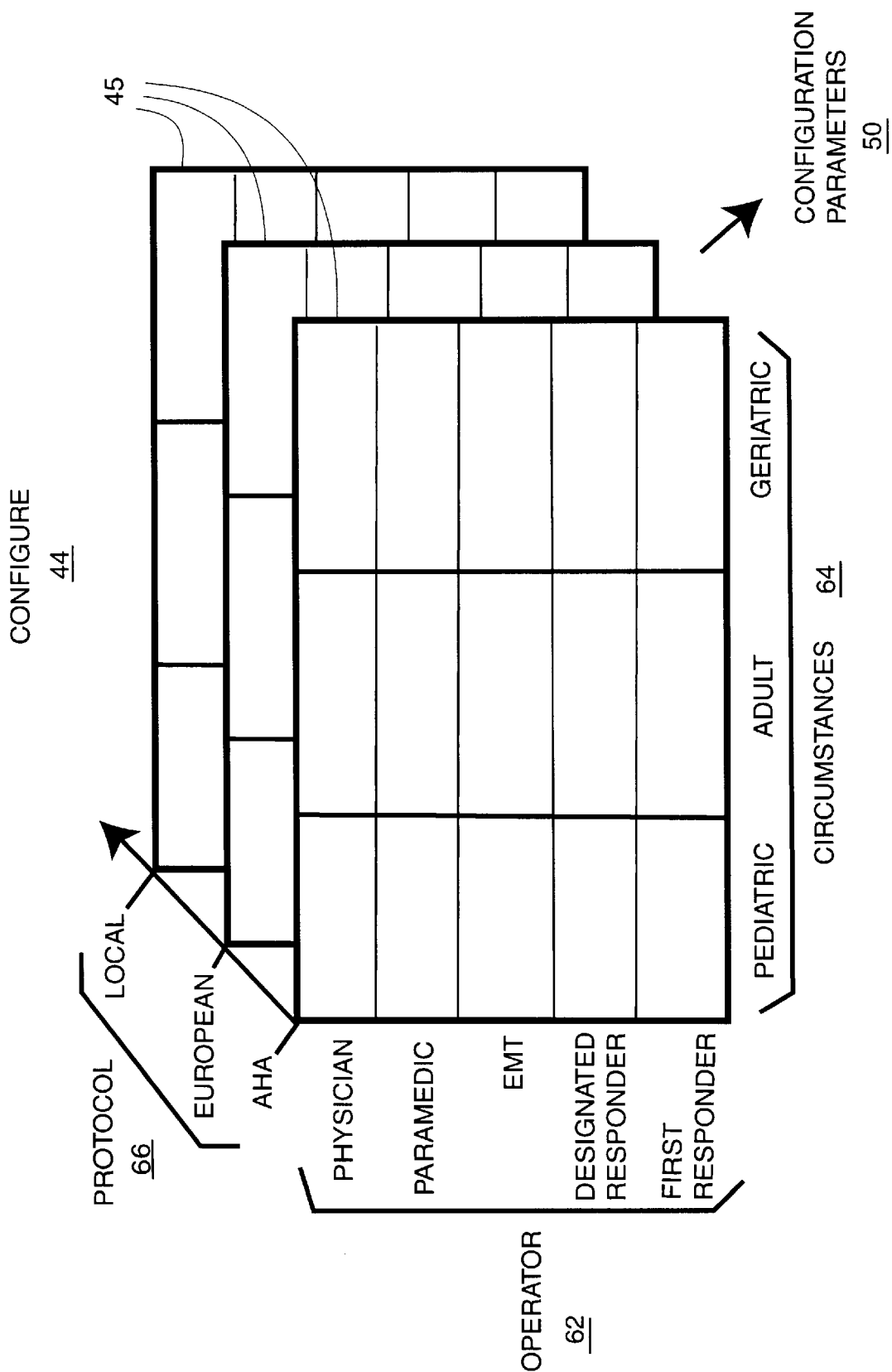
FIG. 7 is an illustration showing an example of an embodiment of the configure routine.

FIG. 7 is an illustration showing an example of the operation of the configure routine 44. As shown in this simplified example, the set of environmental characteristics 60 which includes the protocol 66, operator type 62, and patient age 70 are provided as inputs to a matrix 45 containing various sets of configuration parameters 50. Based on this mapping structure, an appropriate set of configuration parameters is selected and provided to the defibrillator 10. If more elements are added to the set of environmental characteristics 60, an n-dimensional matrix may be constructed to accommodate the additional elements. Other methods of selecting an appropriate set of configuration parameters such as using decision tree structures, look up tables and data bases may be readily applied.

Constructing the matrix or data base within the configure routine 44 may be done after selection of the set of environmental characteristics 60 and the variables required for each of the set of configuration parameters 50. Many of the choices in defining the matrix 45 may be made on the basis of expert knowledge on which behaviors are optimal for each permutation of the environmental characteristics 60. Other choices may be arrived at through reasonable experimentation to determine an optimal behavior.

Constructing the matrix 45 in this manner has the advantages of forcing choices of defibrillator behavior to be made among the various permutations of environmental characteristics 60 as part of an overall process rather than a series of ad hoc decisions made over time. The information contained in the matrix 45 thus represents the collective knowledge that determines the defibrillator 10 behavior. The embodiment of the configure routine 44 as illustrated in FIG. 7 allows a static mapping of the set of environmental characteristics 60 to the sets of configuration parameters 50 in a fixed and predictable manner and requires relatively little processor power to implement.

Figure 8:
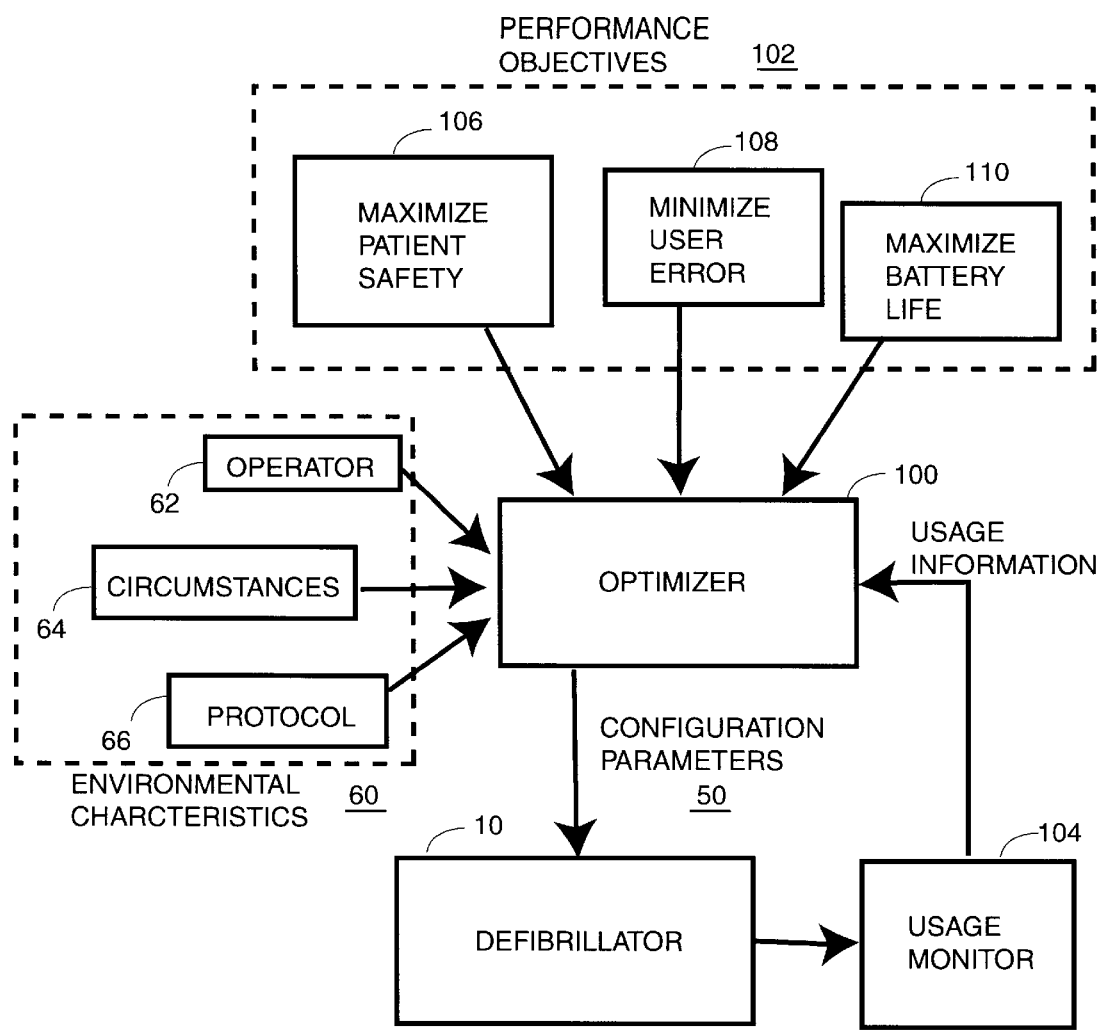
FIG. 8 is a block diagram of an alternative embodiment of the present invention that allows the defibrillator to adapt itself to new environmental characteristics.

FIG. 8 is a block diagram of the method and apparatus for configuring the defibrillator 10 according to alternative embodiment of the present invention. The set of configuration parameters 50 are generated responsive to the set of environmental characteristics 60 which are provided to an optimizer 100. The optimizer 100 performs the functions of the configure routine 44 based on the set of environmental characteristics 60. In addition, a set of performance objectives 102 are provided to the optimizer 100 to further refine the behavior of the defibrillator 10 based on usage information that is measured by a usage monitor 104. The set of performance objectives 102 may include a set of goals that are conflicting or require trade-offs. As shown, the set of performance objectives include goals 106, 108, and 110 labeled "Maximize Patient Safety", "Minimize User Error", and "Maximize Battery Life".

The usage monitor 104 should be capable of providing a measure of the patterns of usage of the defibrillator 10 to allow for optimization of each of the goals 106–110. For example, the usage monitor 104 can be used to measure the duty cycle of the defibrillator 10. In the hospital emergency department, the defibrillator 10 may be used weekly while in a first responder environment the defibrillator 10 may not be used for years. The usage monitor 104 can determine such a pattern of use and optimize the behavior of the defibrillator 10 for the goal 110 of maximizing battery life. For example, the frequency of self test operations, which consume a substantial amount of energy from the battery 24, can be reduced based on a low duty cycle of use determined by the usage monitor 104.

As a further example, the usage monitor 104 can be used to monitor a pattern of inputs during actual use of the defibrillator 10. Multiple erroneous key presses may indicate confusion by the user 12 that can be detected by the usage monitor 104 and provided to the optimizer 100. The frequency and types of prompts from the user interface 42 can be altered to provide further detail in order to optimize the goal of minimizing user error. The usage monitor 104 can also be coupled to a shock advisory algorithm within the controller 26 which provides an indication of the level of artifact present in the ECG signal which may indicate the patient is being moved or CPR is in progress. The goal 106 of maximizing patient safety could be optimized by changing the parameters of the shock advisory algorithm to a more robust standard from a more aggressive standard.

The optimizer 106 is an algorithm that may be implemented through a variety of techniques including fuzzy logic, neural networks, and other non-linear control programs. Fuzzy logic, for example, is particularly suitable for describing human decision making process which cannot be precisely described in conventional mathematical terms. For reasoning purposes, numeric variables are mapped onto a fuzzy set of linguistic variables by a set of membership functions which permit replacing the original numeric measurement by confidences attached to each linguistic term. For example, the usage pattern during actual use of the defibrillator can be mapped into the linguistic variables "skilled operator", "semi-skilled operator", or "confused operator" based on the pattern of operation determined by the usage monitor. The usage pattern could be mapped into the linguistic variables "frequent" and "non-frequent". Rules could then be written such as "If the operator is confused and the usage pattern is infrequent, then maximize the level of prompting." In this way, the defibrillator 10 may provide for optimization of its behavior based on the set of environmental characteristics 60 and also on the set of performance objectives 102.

It will be obvious to those having ordinary skill in the art that many changes may be made in the details of the above-described preferred embodiments of the invention without departing from the spirit of the invention in its broader aspects. The present invention may be applied to any medical device which entails complex configuration parameters in order to adapt to differing environmental characteristics. Therefore, the scope of the present invention should be determined by the following claims.

What we claim as our invention is:

1. A method for configuring a medical device, comprising:

identifying a set of environmental characteristics;

applying said set of environmental characteristics to a configure routine;

determining a set of configuration parameters using said configure routine;

downloading said set of configuration parameters to said medical device; and configuring said medical device with said set of configuration parameters.

2. A method for configuring a medical device, comprising:

identifying a set of environmental characteristics;

applying said set of environmental characteristics to a configure routine;

determining a set of configuration parameters using said configure routine by selecting said set of configuration parameters from a look up table according to said set of environmental characteristics; and configuring said medical device with said set of configuration parameters.

3. A method for configuring a medical device, comprising:

identifying a set of environmental characteristics;

applying said set of environmental characteristics to a configure routine;

determining a set of configuration parameters using said configure routine, applying said set of environmental characteristics to an optimizer, applying a set of performance objectives to said optimizer, monitoring usage patterns with a usage monitor to generate usage information, applying said usage information to said optimizer, and optimizing said set of configuration parameters in said optimizer according to said set of environment characteristics, said set of performance objectives, and said usage information; and configuring said medical device with said set of configuration parameters.

4. A method for configuring a medical device according to claim 3, wherein said optimizer is implemented with fuzzy logic.

5. A method for configuring a medical device according to claim 3, wherein said optimizer is implemented as a neural network.

6. A method for configuring a medical device according to claim 3, wherein said optimizer is implemented as a non-linear control system.

7. A defibrillator configurable for an optimal behavior comprising:

a user interface for receiving a set of environmental characteristics comprising a protocol;

a configure routine coupled to said user interface to receive said environmental characteristics to produce a set of configuration parameters; and a memory coupled to said user interface and said configure routine to receive said configuration parameters to obtain said optimal behavior.

8. A defibrillator configurable for an optimal behavior, comprising:

a user interface for receiving a set of environmental characteristics;

a configure routine coupled to said user interface, said configure routine comprising an optimizer to receive said environmental characteristics and a set of performance objectives to produce a set of configuration parameters, said configure routine further comprising a usage monitor coupled to said defibrillator to generate usage information and to said optimizer to supply said usage information, wherein said optimizer optimizes said set of configuration parameters according to said set of environment characteristics, said set of performance objectives, and said usage information; and a memory coupled to said user interface and said configure routine to receive said configuration parameters to obtain said optimal behavior.

9. A defibrillator configurable for an optimal behavior according to claim 8, wherein said optimizer is implemented with fuzzy logic.

10. A defibrillator configurable for an optimal behavior according to claim 8, wherein said optimizer is implemented as a neural network.

11. A defibrillator configurable for an optimal behavior according to claim 8, wherein said optimizer is implemented as a non-linear control system.

12. A method for configuring a medical device, comprising:

identifying a set of environmental characteristics comprising operator type, circumstances, and protocol;

applying said set of environmental characteristics to a configure routine;

determining a set of configuration parameters using said configure routine; and configuring said medical device with said set of configuration parameters.

13. A method for configuring a medical device according to claim 12, wherein said circumstances comprise a patient age, transport time, and type of arrest.

14. A method for configuring a medical device according to claim 12, wherein said medical device comprises a defibrillator.

15. A method for configuring a medical device according to claim 12, said identifying step further comprising entering said environmental characteristics via a user interface.

16. A method for configuring a medical device according to claim 12, said identifying step further comprising obtaining said environmental characteristics from dispatch data.

17. A defibrillator configurable for an optimal behavior comprising:

a user interface for receiving a set of environmental characteristics comprising operator type and circumstances;

a configure routine coupled to said user interface to receive said environmental characteristics to produce a set of configuration parameters; and a memory coupled to said user interface and said configure routine to receive said configuration parameters to obtain said optimal behavior.

18. A defibrillator configurable for an optimal behavior according to claim 17, wherein said circumstances comprise a patient age.

19. A defibrillator configurable for an optimal behavior according to claim 17, wherein said circumstances comprise an arrest type.

20. A defibrillator configurable for an optimal behavior according to claim 17, wherein said environmental characteristics are entered via said user interface.

21. A defibrillator configurable for an optimal behavior according to claim 17, wherein said environmental characteristics are obtained from dispatch data.

* * * * *